US006355809B1

(12) United States Patent
Chantreux et al.

(10) Patent No.: US 6,355,809 B1
(45) Date of Patent: Mar. 12, 2002

(54) METHOD FOR PREPARING (2S)-1-(2R3S)-5-CHLORO-3-(2-CHLOROPHENYL) -1-(3,4-DIMETHOXY BENZENE-SULPHONYL) 3-HYDROXY-2,3-DIHYDRO-1H-INDOLE-2-CARBONYL PYRROLIDINE-2-CARBOXAMIDE

(75) Inventors: Dominique Chantreux, Montpellier; Philippe Mercey, Valflaunes, both of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/831,721

(22) PCT Filed: Nov. 10, 1999

(86) PCT No.: PCT/FR99/02759

§ 371 Date: May 14, 2001

§ 102(e) Date: May 14, 2001

(87) PCT Pub. No.: WO00/29405

PCT Pub. Date: May 25, 2000

(30) Foreign Application Priority Data

Nov. 16, 1998 (FR) .............................. 98/14384

(51) Int. Cl.[7] ...................... C07D 209/04; C07D 401/06
(52) U.S. Cl. ...................... 548/468; 548/491; 548/484
(58) Field of Search ................................ 548/491, 469, 548/468

(56) References Cited

U.S. PATENT DOCUMENTS

| 5,338,755 A | * | 8/1994 | Wagnon et al. | ............. 514/414 |
| 5,397,801 A | * | 3/1995 | Wagnon et al. | ............. 514/418 |
| 5,481,005 A | * | 1/1996 | Wagnon et al. | ............. 548/537 |
| 5,578,633 A | | 11/1996 | Wagnon et al. | ............. 514/418 |

OTHER PUBLICATIONS

Derwent Patent Abstract No. 199832.

* cited by examiner

*Primary Examiner*—Floyd D. Higel
*Assistant Examiner*—Kamal Saeed
(74) *Attorney, Agent, or Firm*—Paul E. Dupont; Micheal D. Alexander

(57) ABSTRACT

An improved process for preparing (2S)-1-[(2R,3S)-5-chloro-3-(2-chlorophenyl)-1-(3,4-dimethoxybenzenesulphonyl)-3-hydroxy-2,3-dihydro-1H-indole-2-carbonyl]pyrrolidine-2-carboxamide by cyclization of (2S)-1-{[[4-chloro-2-(2-chlorobenzoyl)phenyl]-(3,4-dimethoxybenzenesulphonyl)amino]acetyl}pyrrolidine-2-carboxamide in the presence of an alkali metal hydroxide in a mixture of polyethylene glycol and water.

27 Claims, No Drawings

METHOD FOR PREPARING (2S)-1-(2R3S)-5-CHLORO-3-(2-CHLOROPHENYL) -1-(3,4-DIMETHOXY BENZENE-SULPHONYL) 3-HYDROXY-2,3-DIHYDRO-1H-INDOLE-2-CARBONYL PYRROLIDINE-2-CARBOXAMIDE

This application is a 371 of PCT/FR99/102759 filed Nov. 10, 1999.

The present invention relates to a novel process for the preparation of (2S)-1-[(2R,3S)-5-chloro-3-(2-chlorophenyl)-1-(3,4-dimethoxybenzenesulfonyl)-3-hydroxy-2,3-dihydro-1H-indole-2-carbonyl]pyrrolidine-2-carboxamide, of its solvates and/or of its hydrates.

(2S)-1-[(2R,3S)-5-Chloro-3-(2-chlorophenyl)-1-(3,4-dimethoxybenzenesulfonyl)-3-hydroxy-2,3-dihydro-1H-indole-2-carbonyl]pyrrolidine-2-carboxamide, of formula:

(I)

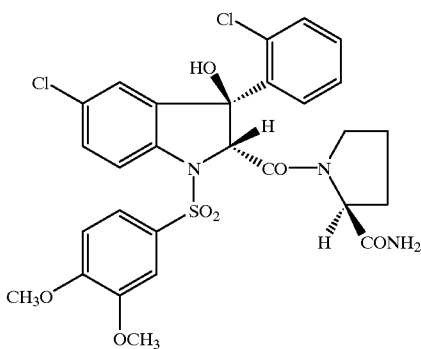

hereinafter known as compound A, is to date the most powerful and the most selective nonpeptide antagonist of arginine-vasopressin $V_{1a}$ receptors in various species, in particular of human $V_{1a}$ receptors (C. Serradeil-Le Gal et al., J. Clin. Invest., 1993, 92, 224–231), and is consequently of use in particular in the treatment of ailments of the cardiovascular system, of the central nervous system, of the renal system or of the gastric system and as antiemetic or antiproliferative agent or, in women, for treating dysmenorrhea or premature labor.

The preparation of compound A is illustrated in Patent EP 0 526 348 or U.S. Pat. No. 5,338,755. According to these documents, compound A is prepared by the cyclization reaction, in basic medium, of the compound of formula:

(II)

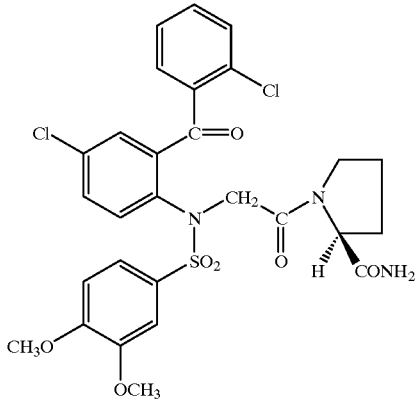

hereinafter known as compound B.

This reaction, related to an aldolization reaction, results in the formation of the compound of formula:

(III)

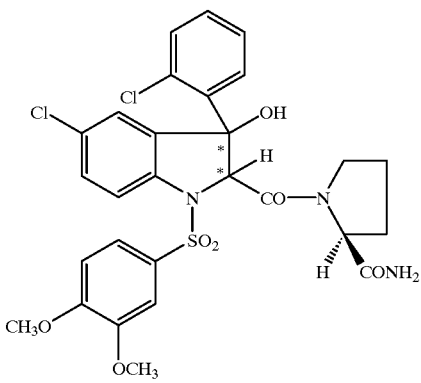

which, because of the formation of two centers of chirality at the 2- and 3-positions of the 2,3-dihydro-1H-indole ring, is found, at the end of the reaction, in the form of a mixture in the reaction medium of the four optical isomers.

This mixture is composed of two optical isomers, conventionally referred to as cis isomers, having the H and OH substituents on the same side of the ring, and of two optical isomers, conventionally referred to as trans isomers, having the H and OH substituents on either side of the ring.

Each of the cis optical isomers is distinguished and characterized in accordance with the analytical methods and process disclosed in document EP 0 526 348. An X-ray analysis made it possible to define the absolute configuration of one of the cis optical isomers, that of the other cis optical isomer being deduced therefrom.

Likewise, each of the trans optical isomers was isolated and characterized. However, their absolute configuration was not determined.

Thus, the four optical isomers of the compound of formula (III) have the following physicochemical characteristics and their conventionally attributed names are shown.

Cis Isomer 1

M.p.=190° C.

$\alpha_D^{20}$=+115° (c=0.305, chloroform)

absolute configuration.

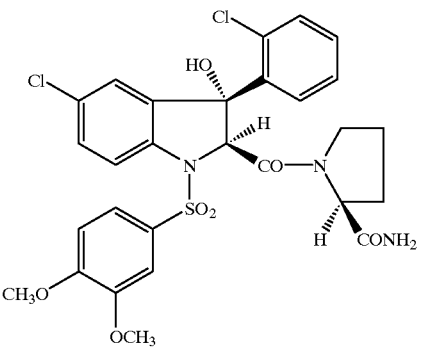

Cis Isomer 2: Compound A

M.p.=154–162° C.

$\alpha_D^{20}$=−216° (c=1.0, chloroform)

absolute configuration.

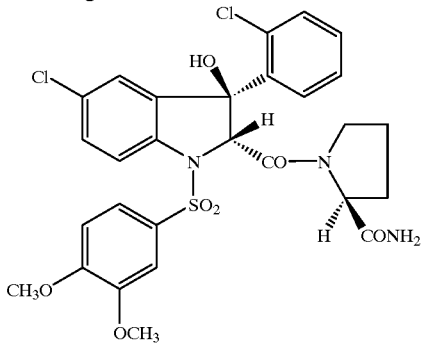

Trans Isomer 1
  $\alpha_D^{20} = +91°$ (c=0.03, chloroform)
  unattributed absolute configuration.
Trans Isomer 2
  M.p.=159° C.
  unattributed absolute configuration.

More specifically, the process for the preparation of compound A as disclosed in the prior art consists in reacting (2S)-1-{[[4-chloro-2-(2-chlorobenzoyl)phenyl](3,4-dimethoxybenzene-sulfonyl)amino]acetyl}pyrrolidine-2-carboxamide (compound B) with 1,8-diazabicyclo[5.4.0] undec-7-ene in methanol for 60 hours and at a temperature of −10° C. to provide the mixture of the four optical isomers of the compound of formula (III).

However, this process has disadvantages, sometimes sufficient to exclude it from any use on the industrial scale.

For example, compound A prepared by this process is obtained with yields which are not very high. During the implementation of this process, compound A has in fact been obtained with final yields of between 12 and 20%, calculated from compound B.

One of the main reasons for this low yield is the presence in the medium of the four optical isomers at the end of the cyclization reaction on compound B. The content, expressed as % by weight, of each of the four optical isomers present in the medium at the end of reactions carried out under the conditions of the process of the prior art was measured by High Performance Liquid Chromatography (HPLC). The mean values are as follows:

| Cis 1 formed (%) | Cis 2 formed compound A (%) | Trans 1 formed (%) | Trans 2 formed (%) |
| --- | --- | --- | --- |
| 20 | 40 | 20 | 20 |

These results thus show the not insignificant presence of the cis 1, trans 1 and trans 2 isomers.

Consequently, the separation of compound A from this mixture and then its purification require numerous stages which contribute, each time, to a decrease in the final yield of compound A.

Furthermore, this process uses 1,8-diazabicyclo[5.4.0] undec-7-ene as base for carrying out the cyclization, which base is expensive and furthermore toxic, ruling out its use on the industrial scale.

Finally, implementation of this process requires a very long reaction time (60 hours).

Consequently, the search for a process for the preparation of compound A which does not exhibit the disadvantages and drawbacks of the known process of the prior art is of indisputable interest.

A novel process for the preparation of compound A, by reaction of compound B with an alkali metal hydroxide in a polyethylene glycol as a mixture with water, which makes it possible to avoid the disadvantages and drawbacks of the known process of the prior art, has, surprisingly, now been found.

The implementation of the process according to the invention makes it possible, during the cyclization reaction, to greatly reduce the formation of the cis isomer 1 and to enhance the formation of compound A. Thus, at the end of the reaction, amounts of the cis isomer 1 of the order of 0.1 to 7% by weight and amounts of compound A of the order of 45 to 60% by weight are achieved.

The separation and the purification of compound A are found to be facilitated thereby and it has been possible to obtain compound A with final yields of the order of 35 to 55%, calculated with respect to compound B.

Furthermore, the process according to the invention employs cheap and nontoxic compounds and makes it possible to greatly reduce the reaction times.

According to one of its aspects, a subject matter of the present invention is a process for the preparation of (2S)-1-[(2R,3S)-5-chloro-3-(2-chlorophenyl)-1-(3,4-dimethoxybenzenesulfonyl)-3-hydroxy-2,3-dihydro-1H-indole-2-carbonyl]pyrrolidine-2-carboxamide, of its solvates and/or of its hydrates of formula:

(I)

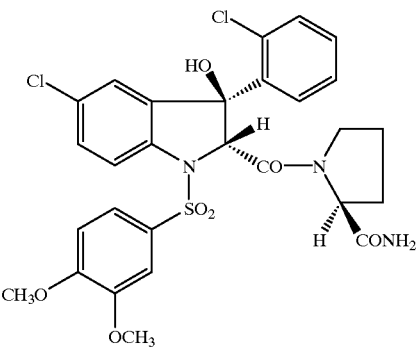

by cyclization reaction of (2S)-1-{[[4-chloro-2-(2-chlorobenzoyl)phenyl](3,4-dimethoxybenzenesulfonyl)-amino]acetyl}pyrrolidine-2-carboxamide of formula:

(II)

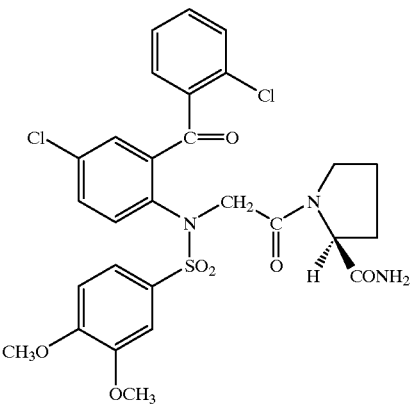

characterized in that the cyclization is carried out by an alkali metal hydroxide in a polyethylene glycol with an average molecular weight of between 200 and 600 as a mixture with water.

The polyethylene glycol (PEG) with an average molecular weight of between 200 and 600 used in the above process can be a polyethylene glycol with a given average molecular weight or alternatively a mixture of polyethylene glycols with varied average molecular weights.

Preference is given, among polyethylene glycols with an average molecular weight of between 200 and 600, to polyethylene glycol 200 or "PEG 200", polyethylene glycol 400 or "PEG 400", or polyethylene glycol 600 or "PEG 600".

Preference is particularly given, according to the invention, to the use of polyethylene glycol 400 or "PEG 400".

The polyethylene glycol/water mixture used in the process of the invention comprises from 0.1 to 1 volume of water per volume of polyethylene glycol. Use is preferably made of a mixture comprising from 0.4 to 0.5 volume of water per volume of polyethylene glycol.

The polyethylene glycol/water mixture is used in a proportion of 2 to 10 equivalents by volume per equivalent by weight of compound of formula (II). The mixture is preferably used in a proportion of 2 to 5 equivalents by volume per equivalent by weight of compound of formula (II).

The alkali metal hydroxide used to carry out the cyclization is chosen from sodium hydroxide, potassium hydroxide or lithium hydroxide. Sodium hydroxide is preferably used.

The alkali metal hydroxide is involved in the reaction in a proportion of 0.1 to 10 molar equivalents per molar equivalent of compound of formula (II), preferably of 0.9 to 1.2 molar equivalents.

The reaction according to the invention is carried out at a temperature of between 0° C. and 45° C. However, a temperature of between 0° C. and ambient temperature (approximately 20 to 25° C.), in particular a temperature of between 0° C. and 17° C., is preferred.

Preferably, at the end of the reaction, the reaction mixture is neutralized, preferably to a pH of between 5.5 and 7.

The neutralization is carried out by addition of an inorganic or organic acid, such as hydrochloric acid, sulfuric acid, potassium hydrogensulfate or acetic acid, to the reaction mixture, said acids being in solution in water or in water in the presence of a water-miscible solvent, such as an alcohol, for example ethanol, and at a temperature of between 0° C. and ambient temperature (approximately from 20 to 25° C.).

The process of the invention thus described takes place over a period of approximately 0.5 to 7 hours.

This time corresponds, under given operating conditions, to the optimum value of the degree of conversion to compound A in the reaction medium being obtained.

It is obvious to a person skilled in the art that this optimum value of the degree of conversion to compound A and the time needed for it to be obtained vary according to the chosen operating conditions.

Compound A, thus obtained according to the process of the invention, can be subsequently separated from the reaction medium according to conventional methods, for example by direct crystallization from the reaction medium after the neutralization stage.

The following nonlimiting examples illustrate the invention. In these examples, the controls during or at the end of the reaction were carried out by HPLC on the reaction medium by taking samples, which are neutralized and diluted in acetonitrile. The results express the content by weight in % of the various compounds present in the reaction medium.

EXAMPLE 1

The cyclization reactions on compound B by one equivalent of lithium hydroxide monohydrate at 20° C. in 4 volume of a PEG 400/water mixture in various volume/volume ratios lead, at the end of the reaction, to the following results:

| PEG 400/H$_2$O (v/v) | Time (min) | Compound B remaining (%) | Cis 1 formed (%) | Cis 2 formed compound A (%) | Trans 1 formed (%) | Trans 2 formed (%) | Impurities (%) |
| --- | --- | --- | --- | --- | --- | --- | --- |
| 60/40 | 30 | 0.2 | 4.9 | 47.4 | 18.2 | 23.0 | 6.3 |
| 70/30 | 60 | 0.4 | 2.8 | 48.7 | 16.5 | 23.5 | 8.1 |
| 80/20 | 120 | 0.1 | 1.3 | 45.7 | 16.7 | 25.2 | 11.0 |

EXAMPLE 2

The cyclization reactions on compound B by 1 equivalent of lithium hydroxide monohydrate in 8 volumes of a PEG 400/water (70/30; v/v) mixture at various temperatures lead, at the end of the reaction, to the following results:

| Temperature (° C.) | Time (min) | Compound B remaining (%) | Cis 1 formed (%) | Cis 2 formed compound A (%) | Trans 1 formed (%) | Trans 2 formed (%) | Impurities (%) |
| --- | --- | --- | --- | --- | --- | --- | --- |
| 0 | 210 | 0.2 | 4.7 | 54.2 | 12.5 | 20.2 | 8.2 |
| 13 | 120 | 0.9 | 3.9 | 49.1 | 15.1 | 23.0 | 8.0 |
| 20 | 60 | 0.4 | 2.8 | 48.7 | 16.5 | 23.5 | 8.1 |
| 40 | 60 | 0.1 | 1.6 | 46.5 | 18.6 | 25.4 | 7.8 |

EXAMPLE 3

The cyclization reactions on compound B, at 0° C. or at 15° C., in 8 volumes of a PEG 400/water (70/30; v/v) mixture by 1 equivalent of various alkali metal hydroxides lead, at the end of the reaction, to the following results:

| Base | Time (min) | Compound B remaining (%) | Cis 1 formed (%) | Cis 2 formed compound A (%) | Trans 1 formed (%) | Trans 2 formed (%) | Impurities (%) |
|---|---|---|---|---|---|---|---|
| at a temperature of 0° C.: | | | | | | | |
| LiOH.H$_2$O | 210 | 0.2 | 4.7 | 54.2 | 12.5 | 20.2 | 8.2 |
| KOH | 420 | 0.6 | 3.3 | 57.5 | 11.1 | 20.9 | 6.0 |
| NaOH | 420 | 0.5 | 2.6 | 60.9 | 12.1 | 19.5 | 4.5 |
| at a temperature of 15° C. | | | | | | | |
| LiOH.H$_2$O | 120 | 0.9 | 3.9 | 49.1 | 15.1 | 23.0 | 8.0 |
| KOH | 30 | 3.2 | 7.4 | 43.3 | 16.6 | 24.4 | 5.1 |
| NaOH | 30 | 1.0 | 5.3 | 47.9 | 13.3 | 27.6 | 4.9 |

EXAMPLE 4

Cyclization reactions on compound B by 1 equivalent of sodium hydroxide at 0° C. in 8 volumes of various PEGs as a mixture with water. The base is dissolved in 1.6 volumes of water and, over 15 minutes, run into the solution of compound B in the PEG/water (5.6/0.8; v/v) mixtures cooled to 0° C., in each case. The results at the end of the reaction are as follows:

| PEG/H$_2$O | Time (min) | Compound B remaining (%) | Cis 1 formed (%) | Cis 2 formed compound A (%) | Trans 1 formed (%) | Trans 2 formed (%) | Impurities (%) |
|---|---|---|---|---|---|---|---|
| PEG 200/H$_2$O | 240 | 0 | 2.7 | 54.1 | 10.3 | 22.6 | 10.3 |
| PEG 400/H$_2$O | 167 | 0 | 2.9 | 59.0 | 10.9 | 21.7 | 5.5 |
| PEG 600/H$_2$O | 150 | 0 | 2.4 | 54.7 | 10.8 | 22.6 | 9.5 |

EXAMPLE 5

(2S)-1-[(2R,3S)-5-Chloro-3-(2-chlorophenyl)-1-(3,4-dimethoxybenzenesulfonyl)-3-hydroxy-2,3-dihydro-1H-indole-2-carbonyl]pyrrolidine-2-carboxamide 32.429 kg of compound B and then 128.0 kg of PEG 400 are charged to a jacketed reactor and left to stir vigorously for 10 minutes at ambient temperature. 16.5 liters of purified water are then run in and the mixture is cooled to 0° C. by circulation of brine in the jacket. A solution of 2.108 kg of sodium hydroxide pellets in 32.5 liters of purified water, cooled beforehand to a temperature of between 15 and 20° C., is subsequently run in slowly and evenly over 1 hour 45 minutes while maintaining the temperature of the medium between 0 and 2° C. After the solution has finished being run in, the mixture is left to stir for 15 minutes at a temperature of between 0 and 2° C.

HPLC control gives the following results:

| Compound B remaining (%) | Cis 1 formed (%) | Cis 2 formed compound A (%) | Trans 1 formed (%) | Trans 2 formed (%) | Impurities (%) |
|---|---|---|---|---|---|
| 17.56 | 4.39 | 47.12 | 9.49 | 19.45 | 1.99 |

The temperature of the reaction medium is raised to 15–17° C. by circulation of cold water in the jacket and the mixture is left to stir for 1 hour at this temperature.

HPLC control shows that the mixture at the end of the reaction comprises:

| Compound B remaining (%) | Cis 1 formed (%) | Cis 2 formed compound A (%) | Trans 1 formed (%) | Trans 2 formed (%) | Impurities (%) |
|---|---|---|---|---|---|
| — | 1.01 | 59.33 | 13.53 | 25.31 | 0.82 |

The pH of the reaction medium is brought to 6, while maintaining the temperature at 20° C., by running in, over 40 minutes, a solution, cooled beforehand to 20° C., comprising 5.4 kg of a 35% solution of hydrochloric acid in water, 113.5 liters of water and 211 liters of ethanol denatured with toluene.

The reaction medium is brought to reflux (T=81.1° C.) and left to stir at reflux for 10 minutes. The medium is cooled to 55° C., seeded by addition of a suspension of 0.391 kg of compound A in 1 liter of water and maintained at 54–55° C. with minimum stirring for 1 hour. The temperature of the medium is gradually brought to 20° C. with a cooling gradient of 10° C./hour and with minimum stirring and then the medium is left to stir overnight at 20–22° C. The reaction medium is cooled to 10° C., the suspended compound A is filtered off and the product obtained is washed twice with 32 liters of an ethanol denatured with toluene/purified water (70/30; v/v) solution and dried under vacuum at 80° C.

In this way, 17.860 kg of compound A are obtained in the form of a white powder.

Yield: 55.07%

HPLC purity: 99.5%.

What is claimed is:

1. A process for the preparation of (2S)-1-[(2R,3S)-5-chloro-3-(2-chlorophenyl)-1-(3,4-dimethoxybenzenesulfonyl)-3-hydroxy-2,3-dihydro-1H-indole-2-carbonyl]pyrrolidine-2-carboxamide of the formula:

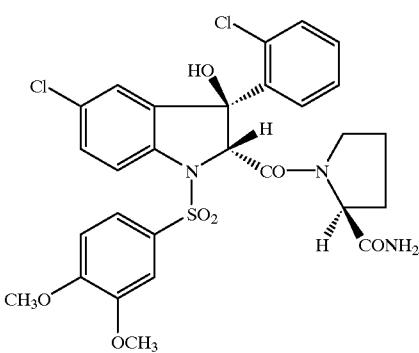

(I)

or a solvate or hydrate thereof by cyclizing of (2S)-1-{[[4-chloro-2-(2-chlorobenzoyl)phenyl](3,4-dimethoxybenzenesulfonyl)amino]acetyl}pyrrolidine-2-carboxamide of the formula:

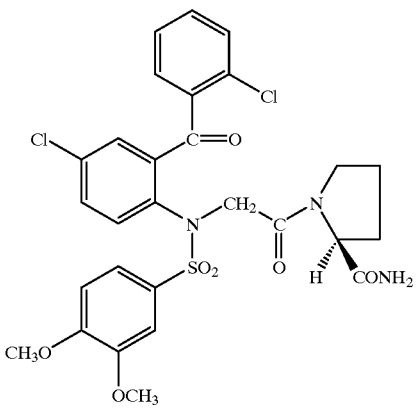

(II)

in the presence of an alkali metal hydroxide in a mixture of water and a polyethylene glycol with an average molecular weight of between 200 and 600, wherein the reaction is carried out at a temperature of between 0° C. and 45° C.

2. A process according to claim 1 wherein the polyethylene glycol with an average molecular weight of between 200 and 600 is a polyethylene glycol with a given average molecular weight or a mixture of polyethylene glycols with varied average molecular weights.

3. A process according to claim 2 wherein the polyethylene glycol with an average molecular weight of between 200 and 600 is polyethylene glycol 200, polyethylene glycol 400 or polyethylene glycol 600.

4. A process according to claim 3 wherein the polyethylene glycol with an average molecular weight of between 200 and 600 is polyethylene glycol 400.

5. A process according to claim 1 wherein the polyethylene glycol/water mixture comprises from 0.1 to 1 volume of water per volume of polyethylene glycol.

6. A process according to claim 5 wherein the polyethylene glycol/water mixture comprises from 0.4 to 0.5 volume of water per volume of polyethylene glycol.

7. A process according to claim 1 wherein the polyethylene glycol/water mixture is used in a proportion of 2 to 10 equivalents by volume per equivalent by weight of compound of formula (II).

8. A process according to claim 7 wherein the polyethylene glycol/water mixture is used in a proportion of 2 to 5 equivalents by volume per equivalent by weight of compound of formula (II).

9. A process according to claim 1 wherein the alkali metal hydroxide is sodium hydroxide, potassium hydroxide or lithium hydroxide.

10. A process according to claim 9 wherein the alkali metal hydroxide is sodium hydroxide.

11. A process according to claim 1 wherein the alkali metal hydroxide is used in a proportion of 0.1 to 10 molar equivalents per molar equivalent of compound of formula (II).

12. A process according to claim 11 wherein the alkali metal hydroxide is used in a proportion of 0.9 to 1.2 molar equivalents per molar equivalent of compound of formula (II).

13. A process according to claim 1 wherein the reaction is carried out at a temperature of between 0° C. and ambient temperature.

14. A process according to claim 13 wherein the reaction is carried out at a temperature of between 0° C. and 17° C.

15. A process according to claim 1 wherein, at the end of the reaction, the reaction mixture is neutralized to a pH of between 5.5 and 7.

16. A process according to claim 3 wherein the polyethylene glycol/water mixture comprises from 0.1 to 1 volume of water per volume of polyethylene glycol.

17. A process according to claim 16 wherein the polyethylene glycol/water mixture is used in a proportion of 2 to 10 equivalents by volume per equivalent by weight of compound of formula (II).

18. A process according to claim 17 wherein the alkali metal hydroxide is sodium hydroxide, potassium hydroxide or lithium hydroxide.

19. A process according to claim 18 wherein the alkali metal hydroxide is used in a proportion of 0.1 to 10 molar equivalents per molar equivalent of compound of formula (II).

20. A process according to claim 19 wherein the reaction is carried out at a temperature of between 0° C. and ambient temperature.

21. A process according to claim 20 wherein, at the end of the reaction, the reaction mixture is neutralized to a pH of between 5.5 and 7.

22. A process according to claim 4 wherein the polyethylene glycol/water mixture comprises from 0.4 to 0.5 volume of water per volume of polyethylene glycol.

23. A process according to claim 22 wherein the polyethylene glycol/water mixture is used in a proportion of 2 to 5 equivalents by volume per equivalent by weight of compound of formula (II).

24. A process according to claim 23 wherein the alkali metal hydroxide is sodium hydroxide.

25. A process according to claim 24 wherein the alkali metal hydroxide is used in a proportion of 0.9 to 1.2 molar equivalents per molar equivalent of compound of formula (II).

26. A process according to claim 25 wherein the reaction is carried out at a temperature of between 0° C. and 17° C.

27. A process according to claim 26 wherein, at the end of the reaction, the reaction mixture is neutralized to a pH of between 5.5 and 7.

* * * * *